(12) United States Patent
Hossack et al.

(10) Patent No.: US 6,352,511 B1
(45) Date of Patent: Mar. 5, 2002

(54) MEDICAL DIAGNOSTIC ULTRASOUND SYSTEM AND METHOD FOR POST PROCESSING

(75) Inventors: John A. Hossack, Palo Alto; Samuel H. Maslak, Woodside; Kutay F. Ustuner, Mountain View; Mirsaid Seyed-Bolorforosh, Portola Valley, all of CA (US)

(73) Assignee: Acuson Corporation, Mountain View, CA (US)

(*) Notice: Subject to any disclaimer, the term of this patent is extended or adjusted under 35 U.S.C. 154(b) by 0 days.

(21) Appl. No.: 09/777,691

(22) Filed: Nov. 2, 2000

Related U.S. Application Data

(62) Division of application No. 09/328,312, filed on Jun. 8, 1999.

(51) Int. Cl.[7] .................................................. A61B 8/00
(52) U.S. Cl. ........................................ 600/443; 600/458
(58) Field of Search .......................... 600/437, 441–447, 600/454–458, 453

(56) References Cited

U.S. PATENT DOCUMENTS

| | | |
|---|---|---|
| 5,215,094 A | 6/1993 | Franklin et al. |
| 5,235,984 A | 8/1993 | D'Sa |
| 5,249,578 A | 10/1993 | Karp et al. |
| 5,467,770 A | 11/1995 | Smith et al. |
| 5,479,926 A | 1/1996 | Ustuner et al. |
| 5,579,768 A | 12/1996 | Klesenski |
| 5,595,179 A | 1/1997 | Wright et al. |
| 5,653,235 A | 8/1997 | Teo |
| 5,720,291 A | 2/1998 | Schwartz |
| 5,788,635 A | 8/1998 | Wright et al. |
| 5,795,297 A | 8/1998 | Daigle |
| 5,833,613 A | * 11/1998 | Averkiou et al. ........... 600/440 |
| 5,873,830 A | 2/1999 | Hossack et al. |
| 5,899,863 A | 5/1999 | Hatfield et al. |
| 5,904,653 A | 5/1999 | Hatfield et al. |
| 5,908,389 A | 6/1999 | Roundhill et al. |
| 5,951,478 A | * 9/1999 | Hwang et al. .............. 600/443 |
| 6,095,980 A | 8/2000 | Burns et al. |

* cited by examiner

*Primary Examiner*—Peter Vo
*Assistant Examiner*—Ali M. Imam
(74) *Attorney, Agent, or Firm*—Craig A. Summerfield; Brinks Hofer Gilson & Lione

(57) ABSTRACT

Ultrasound data is generated by a receive beamformer. Ultrasound image processing is applied to the ultrasound data for presentation of an image. Various ones of the ultrasound image processing steps may be reversed. For example, persistence processing may be reversed in order to obtain ultrasound data associated with data prior to persistence processing. This recovered data may be used to generate an image or for application of a different amount of persistence. Other processes that may be reversed to recover ultrasound data include focal and depth gain compensation, dynamic range compression, intensity or color mapping, and various filtering, such as persistence or spatial filtering.

17 Claims, 3 Drawing Sheets

MEDICAL DIAGNOSTIC ULTRASOUND SYSTEM AND METHOD FOR POST PROCESSING

This application is a division of application Ser. No. 09/328,312, filed Jun. 8, 1999, (pending), the disclosure of which is incorporated herein by reference.

BACKGROUND

This invention relates to a medical diagnostic ultrasound system and method for post-processing. In particular, a system and method for removing the effects of persistence and other post-processing is provided.

Ultrasound systems transmit acoustic waveforms and generate ultrasound data representing echo signals along a plurality of scanlines. The ultrasound data provided by receive beamformers undergoes various processes to generate an image on a display. These processes include focal gain compensation, dynamic range adjustment, various forms of filtering, display gray level mapping, and depth gain compensation.

For example, persistence processing or filtering is performed. Typically, an infinite impulse response (IIR) filter filters ultrasound data samples representing the same location at different times. This data is filtered as a function of one filter coefficient, typically labeled alpha ($\alpha$). The amount of persistence may be changed as a function of the filter coefficient.

Ultrasound data altered by the various ultrasound image processes discussed above is used to generate an image and may be output to other devices, such as remote viewing stations or temporary or semi-permanent image storage memory. The ultrasound data is formatted for transfer to remote viewing stations. For example, the DICOM format is used. Pursuant to this format, the processed ultrasound data is provided with information indicating the patient, time of examination and various parameters indicating the type and amount of processing used to generate the transferred ultrasound data. Some of these descriptors are standard and some are added as proprietary variants. Processors at the remote viewing station use the ultrasound data to generate an image. The patient information and processing information is also displayed with the image. However, imaging the same region of the same patient with a different amount or types of ultrasound image processing may require the patient to be scanned again, requiring an expensive and inconvenient repeat examination.

BRIEF SUMMARY OF THE INVENTION

The present invention is defined by the following claims, and nothing in this section should be taken as a limitation on those claims. By way of introduction, the preferred embodiment described below includes a medical diagnostic ultrasound method and system for processing ultrasound data. Ultrasound data is generated by a receive beamformer. Ultrasound image processing is applied to the ultrasound data for presentation of an image. Various ones of the ultrasound image processing steps may be reversed. For example, persistence processing may be reversed in order to obtain ultrasound data associated with data prior to persistence processing. This recovered data may be used to generate an image or for application of a different amount of persistence. Other processes that may be reversed to recover ultrasound data include focal and depth gain compensation, dynamic range compression, intensity or color mapping, and various filtering steps, such as persistence or spatial filtering.

In one embodiment described below, the recovery of ultrasound data through the reversal of various ultrasound image processes is performed by a remote work station. The remote work station is provided with various parameters representing the type and amount of ultrasound image processing used to generate the ultrasound data. Based on this information, the remote viewing station recovers the ultrasound data. In other embodiments, the ultrasound data is processed to estimate the amount of ultrasound image processing. The estimates are then used to recover ultrasound data through reversal of the ultrasound image processing.

In one aspect, a medical diagnostic ultrasound system and method for processing ultrasound data is provided. A beamformer obtains ultrasound data. At least one of various processors or other devices ultrasound image process the ultrasound data in response to at least one ultrasound image processing parameter. A processor reverses at least some of the ultrasound image processing as a function of the ultrasound image processing parameter.

In a second aspect, a medical diagnostic ultrasound system and method for persistence processing is provided. At least two frames of persisted ultrasound data are obtained. At least two frames of reduced persistence ultrasound data are recovered from the at least two frames of persisted ultrasound data. In further aspects, the reduced persistence ultrasound data is recovered based on either a known persistence coefficient or an estimated persistence filter coefficient.

Further aspects and advantages are discussed below in conjunction with the preferred embodiments.

DETAILED DESCRIPTION OF THE INVENTION

Ultrasound data representing a region of a target at substantially one point in time is acquired as a frame of ultrasound data. One or more frames of ultrasound data are subjected to ultrasound image processing, such as various gain compensation adjustments, dynamic range adjustments, spatial filtering, temporal filtering, and post-processing curve gray level mapping. The processed frames of ultrasound data may be used to generate an image, such as a B-mode or motion image (e.g. Color Doppler image). As an alternative or in addition to display as an image, at least some of the ultrasound image processing is reversed. Ultrasound data associated with less or none of one or more of the types of ultrasound image processing is recovered. By recovering the ultrasound data prior to one or more ultrasound image processing steps, an image or images may be generated based on different ultrasound image processing without having to reacquire the ultrasound data from a patient.

As used herein, ultrasound data broadly encompasses data at any one of various points or stages of processing within an ultrasound system, including electrical signals generated by a transducer in response to echoes, beamformed samples representing a line within the target, coherent or incoherent data, scan-converted data, or data prior to or after any of the various ultrasound image processing steps described herein.

Figure 1:
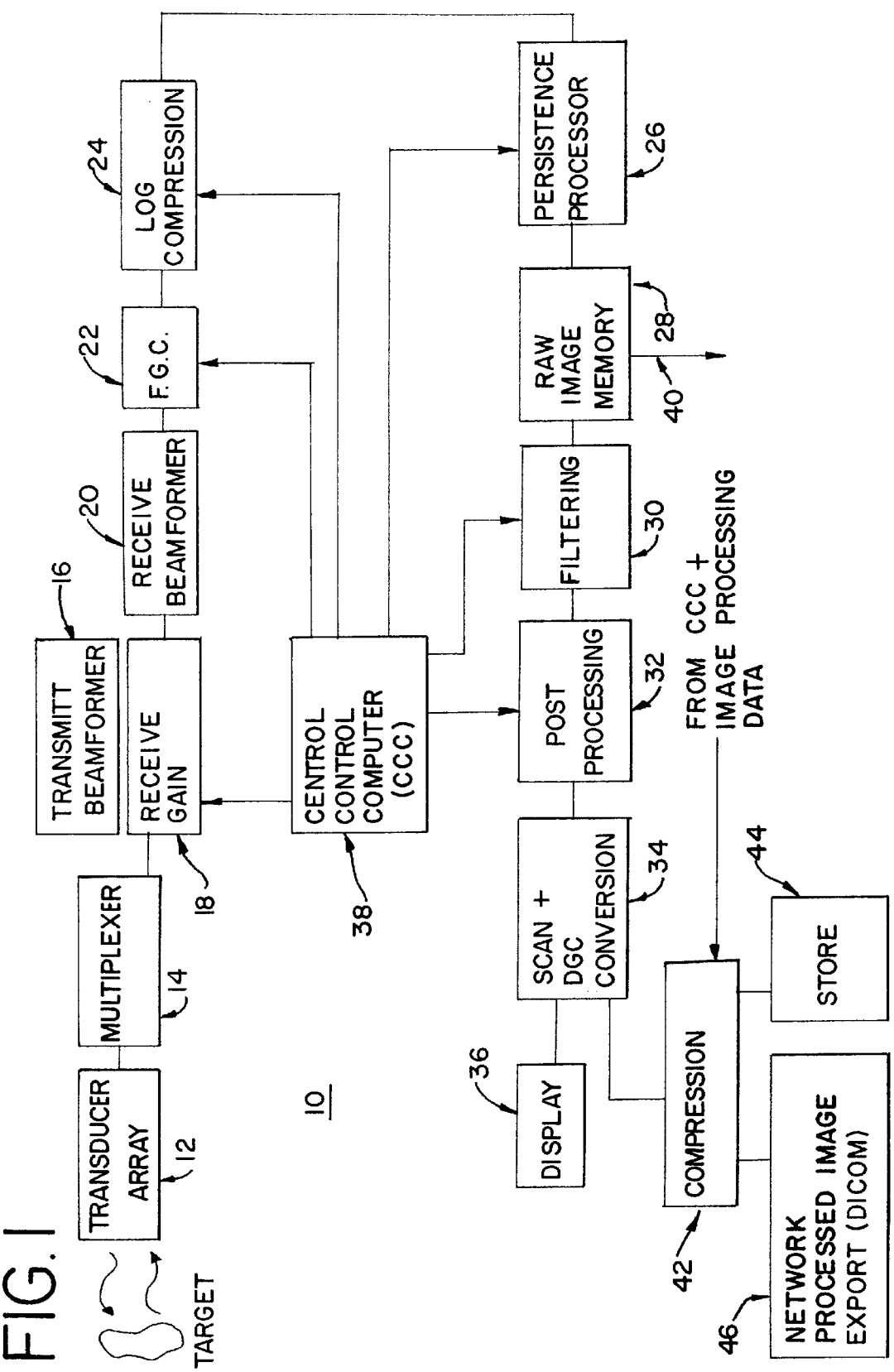
FIG. 1 is a block diagram of one embodiment of a medical diagnostic ultrasound system for processing ultrasound data.

Referring to FIG. 1, one embodiment of a medical diagnostic ultrasound system for acquiring and ultrasound image processing ultrasound data for eventual reversal of at least some of the ultrasound image processing is shown generally at 10. The system 10 may comprise ultrasound systems manufactured under the trade names 128 XP, ASPEN, and SEQUOIA by Acuson Corporation or systems manufactured by other ultrasound manufacturers.

The system 10 includes a transmit beamformer 16 connected through a multiplexer 14 to a transducer array 12. Echoes responsive to transmitted beams are received by the transducer array 12 and passed through the multiplexer 14 to a receive path. The receive path that includes a gain block 18, a receive beamformer 20, a focal gain compensation processor 22, a log compression device 24, a persistence processor 26, a memory 28, a filter 30, a post-processing look-up table 32, a scan converter, and a depth gain compensation processor 34. The system 10 also includes a display connected with the receive path and a central control computer 38 connected to various components of the receive path. Fewer or additional devices for ultrasound image processing may be provided. These devices may also be placed in a different order along the receive path. For example, the memory 28, is placed at any point along the receive path between the receive beamformer 20 and the display 36. The system 10 may comprise analog components, digital components or combinations thereof. In a mechanically scanned system, a single transducer element without a beamformer may be used.

The central control computer 38 comprises one or more processors for controlling the acquisition of ultrasound data and subsequent ultrasound image processing. The central control computer 38 may be independent of, part of or partly a part of the devices for ultrasound image processing.

Ultrasound data is subjected to various ultrasound image processing. The gain block 18 comprises an amplifier, processor, multiplier or other hardware device for amplifying the ultrasound data provided from the transducer array 12 as an ultrasound imaging process. The gain provided by the gain block 18 is adjustable and controlled by the central control computer 38. The gain is adjusted as a function of a predetermined value based on measured or expected signal level or dynamically as a function of the signal-to-noise ratio. The amount of gain or another parameter used to determine the amount of gain comprises an ultrasound image processing parameter.

The amplified data output by the receive gain device 18 is provided to the receive beamformer 20. The receive beamformer 20 comprises a summer and optionally one or more filters. The receive beamformer 20 receives ultrasound data corresponding to a plurality of channels and sums the data. The summed ultrasound data represents the structure or fluid along a line of the target or patient. The receive beamformer 20, under the control of central control computer 38, is used to acquire a frame of ultrasound data associated with the type of imaging desired. For example, a frame of ultrasound data includes data representing a single point or region within the target for spectral Doppler imaging, a single scanline within the target for M-mode imaging, and a plurality of scanlines for two- or three-dimensional B-mode or motion imaging. Each frame of ultrasound data corresponds to substantially one time. A plurality of frames of ultrasound data acquired over time represent a sequence of frames of ultrasound data. The number of frames of ultrasound data acquired over a particular amount of time or within the sequence determines a frame rate.

The focal gain compensation look-up table 22 comprises a RAM or ROM memory device for ultrasound image processing. In alternative embodiments, a processor, multiplier or amplifier is used. Focal gain compensation look-up table 22 applies gain to ultrasound data as a function of a spatial location or proximity to the transmit beam focal point along each scan line. Focal gain compensation ultrasound image processing compensates for the increased energy associated with the focal point as compared to away from the focal point. Ultrasound data is generated with similar amplitudes regardless of the focal point. Focal gain compensation is performed as a function of a focal gain compensation parameter, such as one or more selectable look-up tables of output values given a particular input value for each spatial location along an ultrasound line. Other focal gain compensation parameters may be used, such as magnitude data provided by the central control computer 38 for varying the amplitude as a function of depth. Focal gain compensation may also include gain added to compensate for depth and frequency dependent attenuation. The focal gain compensation parameters are automatically applied based on precalculated data or data generated in real time under the control of the central control computer 38, such as disclosed by Klesenski in U.S. Pat. No. 5,579,768.

The ultrasound data is also provided to the log compression device 24 for further ultrasound image processing. The log compression device 24 comprises a digital signal processor, a processor, a look-up table memory or other device for log compressing the dynamic range of the ultrasound data. The acquired ultrasound data has a high dynamic range and the dynamic range is reduced by the log compression device 24. Log compression is performed in response to a dynamic range parameter. The dynamic range parameter comprises a desired range, such as 50–80 db or other parameter for controlling log compression. Preferably, the log compression device 24 outputs ultrasound data rounded to and represented by eight bits. A different number of bits or analog information may be used for representing the ultrasound data.

The ultrasound data is provided to the persistence processor 26 for further ultrasound image processing. The persistence processor 26 comprises a digital signal processor, a processor, or a filter for filtering through a sequence of ultrasound data (i.e. temporal filtering). In one preferred embodiment, the persistence processor 26 comprises an infinite impulse response (IIR) filter responsive to an IIR filtering parameter α. α controls the weighting applied to the current and previous frames of ultrasound data within the sequence, as mathematically represented below:

$$I_{out}(i) = \alpha * I_{out}(i-1) + (1-\alpha) * I_{in}(i) \qquad (1)$$

where for the $i^{th}$ frame I, $I_{in}$ is the input frame and $I_{out}$ is the output frame. The IIR filtering operation may also use additional inputs, such as $I_{out}(i-2)$. In alternative embodiments, the persistence processor 26 performs finite impulse response (FIR) filtering, and the persistence filtering parameters comprise the type of FIR filter or the number of taps and various weights applied for FIR filtering. The weights applied or the alpha value used represent filter coefficients. The filter coefficients and associated filters may vary as a function of time or location within the frame of ultrasound data.

The persisted ultrasound data is stored in the memory 28. The memory 28 comprises a RAM, hard disk drive, a removable memory medium or other memory device for storing ultrasound data. The memory device 28 may perform CINE functions. Preferably, the memory 28 receives persisted ultrasound data since persistence with IIR filtering is reversible and fully reversible if based on equation (1). The stored ultrasound data may be compressed so that the amount of data is reduced while still allowing for other ultrasound image processing to work in a useful manner. In alternative embodiments, the memory 28 is provided along a different portion of the receive path.

In addition to persistence filtering, spatial filtering is provided by the filter 30 for further ultrasound image processing. The filter 30 comprises a processor, digital signal processor, or filter for implementing one or more of various filters. The various filters include IIR and FIR filtering. The filtering may be linear or nonlinear, and high pass or low pass. High-pass spatial filtering may be used to emphasize edges of structure within the target, and low-pass spatial filtering may be used to emphasize contrast within the target. In other embodiments, the filtering includes the combination of contrast ultrasound data with high resolution ultrasound data, such as taught in U.S. Pat. No. 5,479,926. Any of these various filtering functions are responsive to one or more filtering parameters. For example, the filter coefficients from an IIR or a FIR filter comprise filter parameters. The filter parameters may also include a number taps or spatial distribution of the kernel for spatial filtering. In the filtering taught in U.S. Pat. No. 5,479,926 and possibly other filters, the filtering parameter comprises a look-up table or data for selecting or generating a look-up table. Other filters may be used. For example, using Wiener filter design, an estimate of the noise from the non-signal noise frame of data is determined. Using the non-signal noise frame of data, an estimate of the optimal filter for recovering a relatively noise-free image of ultrasound data is determined. Alternatively, the noise frame is used to determine which portion of the image includes noise, and a filter or mask is applied to the image data to suppress noise in the appropriate portion of the image. For any of these various filters, the filtering and associated filtering parameters may change as a function of depth or azimuthal location. The spatial filters and filtering parameters may also change as a function of time, Such as different spatial filtering for different frames of ultrasound data.

Figure 4:
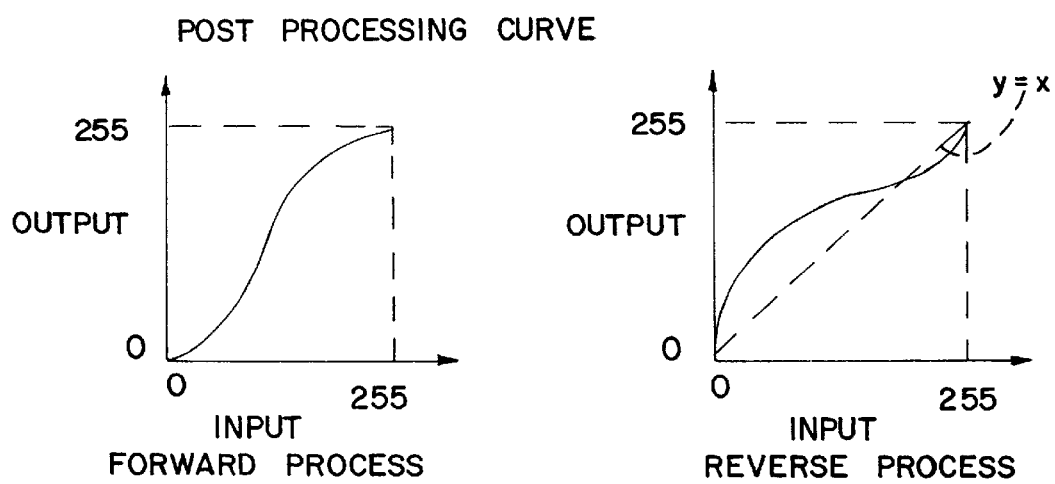
FIG. 4 is a graphical representation of a post-processing curve and that curve's inverse.

The spatially filtered ultrasound data is transformed by the post-processing look-up table 32 as further ultrasound image processing. The post-processing look-up table 32 comprises a RAM or ROM memory device, a digital signal processor, a processor or other device for transforming the input ultrasound data into output ultrasound data to better emphasize data for imaging. The transform is typically represented by an S-shaped curve, such as shown in FIG. 4. This curve de-emphasizes low- and high-intensity data. Other curves may be used. In alternative embodiments, the curves vary as a function of depth and/or azimuthal position. For example, a two-dimensional mapping function is used. The post-processing curve parameter comprises the post-processing curve or data used for selecting or generating the post-processing curve or maps.

The transformed ultrasound data is provided to the scan converter 34. The scan converter comprises a device for reformatting polar coordinate ultrasound data into Cartesian coordinate ultrasound data.

The scan converter 34 may also comprise a RAM or ROM look-up table, processor, digital signal processor or other device for providing depth gain compensation. In one preferred embodiment, the gain applied at any particular depth or range of depths is a function of user input, such as input data provided by the central control computer 38 from user adjusted potentiometers or slides. This depth gain compensation comprises ultrasound image processing. In alternative embodiments, depth gain compensation is automatically controlled, such as disclosed in U.S. Pat. No. 5,579,768, where the depth gain compensation parameters comprise the variables used to determine the gain at different depths. The depth gain parameter may include some or all of focal gain parameters. The gain compensation parameter comprises an amplifier control value, a multiplier value (i.e. weight) or other parameter for adjusting the intensity or magnitude of ultrasound data.

Another ultrasound image processing operation is histogram equalization. The persistence processor 26 or another device described herein performs histogram equalization to create a more uniform histogram of gray scale values. Ultrasound data representing intensities is altered to enhance the contrast of resulting images using histogram equalization. The histogram equalization operation corresponds to a mapping function. This mapping function is stored for determining and applying an inverse function for reversal. The transformation used for histogram equalization may be changed on a frame-by-frame or subset of frames basis. The histogram equalization ultrasound image parameter comprises the histogram equalization transform or an index identifying a particular histogram equalization transform.

While the devices for performing ultrasound image processing have been discussed above as individual or single devices, each may comprise more than one processor or other associated devices. One or more processors, digital signal processors, or look-up tables or other hardware may be used to implement two or more different ultrasound imaging processes. For example, one general processor may operate pursuant to software control for providing two or more of focal gain compensation, log compression, persistence filtering, spatial filtering, application of a processing curve, depth gain compensation, and other ultrasound image processing. Different types of ultrasound image processing, including known and yet to be developed processes, may be included.

The ultrasound data, after any ultrasound image processing, is output to the display 36 for generation of an image. The image is responsive to the various ultrasound image processing, such that adjustment of one or more of the ultrasound imaging processing parameters affects the image generated in response to subsequent frames of ultrasound data. Fewer than all of the ultrasound image processes discussed herein may be used to generate an image.

Ultrasound data used to generate the image on the display 36 and the associated processing parameters are transmitted and/or stored for reversal of at least some of the ultrasound image processing. For example, the scan converted ultrasound data from the scan converter 34 is provided to a compression processor 42. The compression processor 42 comprises a digital signal processor or other processor for compressing data. In one embodiment, JPEG or MPEG compression is used. The compression may be either lossy or a loss less, and may use frequency transformation, sampling, coding (e.g. Huffman coding or RLE run length encoding), frame to frame motion estimation (e.g. to create persistent images), or other compression techniques. The compressed ultrasound data is provided to a network 46 or stored in a memory device 44. The network 46 may comprise the Internet, an intranet or a connection between any two processors. The storage device 44 may comprise a RAM memory, a hard disk drive, a floppy disk drive or other movable storage media. The storage device 44 may comprise a memory device 28. The storage device 44 may comprise a local or a remote memory. Ultrasound data from other parts of the receive path may be input into the compression processor 42. Ultrasound data associated with one or more of various ultrasound image processes may be output from anywhere along the receive path to the compression processor 42. In alternative embodiments, the ultrasound data is not compressed prior to transmission to the network 46 or the storage device 44. Where reversal of ultrasound image processing to recover ultrasound data is performed by the system 10, compression is preferably not performed, but may be. Where reversal is performed by a remote processor, compression is preferably performed prior to transmission of the ultrasound data.

In one preferred embodiment, ultrasound data that is log compressed and temporally persisted without being spatially filtered, transformed pursuant to a post-processing curve, and altered for depth gain compensation is used to reverse the ultrasound image processing associated with one or more of the persistence processing, log compression and focal gain compensation. The persisted ultrasound data is stored in the memory device 28 and provided on an output 40 for transmission to a remote processor. Alternatively, the central control computer 38 or another processor for reversing ultrasound image processing accesses the ultrasound data from the memory device 28 or a removable storage medium.

The data transmitted or stored may comprise one or more of various types of data. For example 16-bit, 8-bit or other amounts of data for each sample may be used. The data may comprise in phase and quadrature data (i.e. complex baseboard demodulated RF data), radio frequency (RF) data, or an intermediate frequency (IF) acoustic data, regardless of any log compression. To account for adaptive or varying ultrasound image process parameters, the parameters stored or transferred with the frames of ultrasound data are transferred with each frame or as a header to a sequence of frames, depending on the frequency of change of any processing parameters.

Preferably, one or more of the various ultrasound image processing parameters are stored with each frame of ultrasound data. For example, the IIR filter coefficient for persistence processing is stored with the frame of ultrasound data. Preferably, ultrasound image processing parameters for each of the ultrasound imaging processes performed on the stored or transmitted ultrasound data are stored or transmitted with that ultrasound data. In the embodiment discussed above where persistence processing has been performed without subsequent ultrasound image processing, the ultrasound image processing parameters associated with focal gain compensation, log compression and persistence processing are stored or transmitted with the ultrasound data.

Alternatives to transmitting or storing the ultrasound image processing parameters may be used. In one alternative, an index or other representation of the ultrasound image processing parameter performed on the ultrasound data is used. For example, a numerical description of the image processing parameters or an index may be used. Where look-up tables or other complex ultrasound image processing parameters are provided, an index method is preferably used. Based on the index value, a known or common look-up table entry (e.g. a look-up table exists or is accessible at both a source and a destination) or other ultrasound image processing parameter may be obtained for reversing the ultrasound image processing. In a second alternative, a frame of data acquired without a transmission step is obtained. This non-signal noise frame is transmitted with the ultrasound data for use in recovering ultrasound data. In a third alternative, the ultrasound image processing parameters are not stored or transmitted with the frames of ultrasound data. The frames of ultrasound data are then used to estimate or determine the ultrasound image processing parameters as discussed below.

In one preferred embodiment, parameters for ultrasound image processing used to generate an image on the display 36 subsequent to the stage of processing used for the stored or transmitted frames of ultrasound data are stored or transmitted with the stored or transmitted ultrasound data. For example, ultrasound data associated with persistence processing is stored in the memory 28. Spatial filtering, post process mapping and depth gain compensation are performed to generate an image. The ultrasound image processing parameters associated with processes before and after storage of the ultrasound data in the memory 28 are stored with or transmitted with the ultrasound data provided from the memory 28. These additional subsequent ultrasound image processing parameters may be used for generating during a later review an image substantially identical to the image that was previously generated on the display 36.

In addition to the ultrasound image processing parameters, other information associated with the frames of ultrasound data is stored and/or transmitted. For example, the frame rate is stored. The frame rate may be used for general information purposes or for reversing persistence processing where persistence is adapted to the frame rate, such as disclosed in U.S. Pat. No. 5,595,179. The actual time of acquisition or a time of acquisition relative to a physiological event or other signal, such as an ECG or injection of a contrast agent, is also stored or transmitted with the frame of ultrasound data. Patient information, including date of birth, social security number, date of acquisition and other information, such as provided for in the DICOM standard, is also provided. The ultrasound data and associated ultrasound image processing parameters and other stored information may be transmitted and/or stored pursuant to the DICOM standard with additional data fields (e.g. proprietary variants) provided as needed. Other formats may be used, such as TIFF or BMP. In alternative embodiments, a proprietary format is used.

Ultrasound data that has been subjected to ultrasound image processing step in response to at least one ultrasound image processing parameter is obtained for recovery of previous ultrasound data. To recover the previous ultrasound data, at least some of the ultrasound image processing is reversed as a function of the ultrasound image processing parameter.

This reversal is performed by a remote system or by the ultrasound system 10. If performed by the ultrasound system 10, the central control computer 38 or another processor obtains stored ultrasound data from the memory 28, the memory 44 or another memory for recovering the previous ultrasound data as discussed below. For recovery by a remote processor, an ultrasound system comprising the remote processor receives the transmitted data or acquires the data from a storage device and performs the reversal of the ultrasound image processing, as discussed below.

Figure 2:
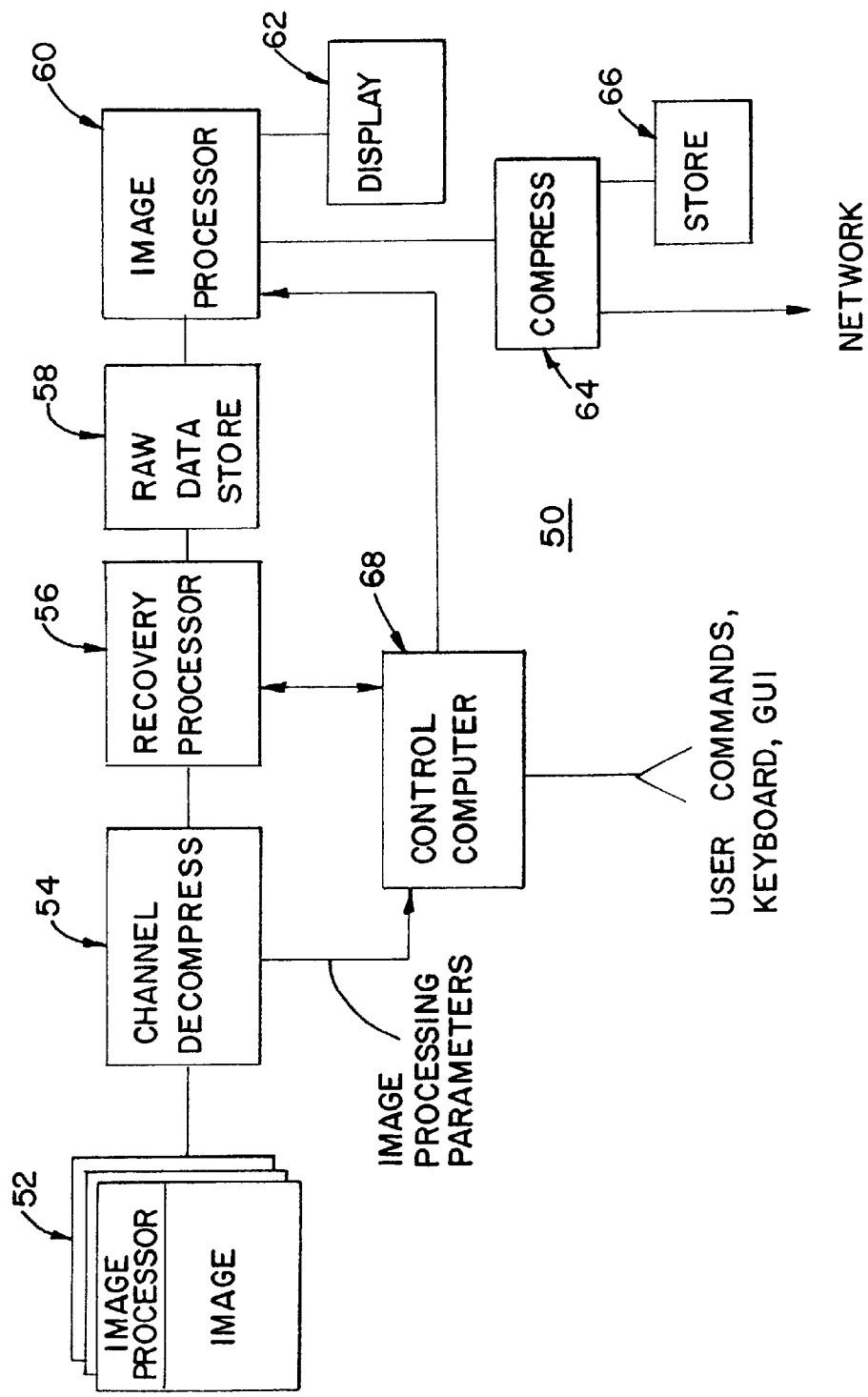
FIG. 2 is a block diagram of another medical diagnostic ultrasound system for processing ultrasound data.

Referring to FIG. 2, one embodiment of a medical diagnostic ultrasound system for reviewing ultrasound images by reversing ultrasound image processing is shown generally at 50. The system 50 comprises components of the ultrasound system 10 of FIG. 1 or components of a remote ultrasound system. For example, the system 50 comprises a picture archiving computer system or other processor, such as an AEGIS ultrasound system manufactured by Acuson Corporation. Other remote systems and processors may be used.

System 50 includes an optional decompression processor 54, a recovery processor 56, a memory device 58, image processor 60, a display 62, an optional compression processor 64, and an optional memory device 66. A control computer 68 controls the operation of these various components. A same device may be used for two or more of the various components of the system 50. For example, the decompression processor 54 and the compression processor 64 may comprise a single digital signal processor. As another example, the recovery processor 56, the image processor 60, and optionally the control computer 68 comprise a single one or a group of processors for performing each of the processes associated with these processors as discussed below.

The system 50 obtains a sequence of frames of ultrasound data as represented by the block 52. The sequence is obtained from a target, from a transmission of ultrasound data or from a storage or memory device. The ultrasound data of the sequence has been previously altered by ultrasound image processing.

If the obtained ultrasound data is compressed, the decompression processor 54 decompresses the data. Preferably, the decompression processor 54 comprises a digital signal processor or other processor for decompressing data, such as JPEG or MPEG decompression processors. In alternative embodiments, the ultrasound data is not compressed or is to remain compressed, so the decompression processor 54 is not provided or is bypassed.

After any decompression, ultrasound image processing is reversed, at least in part, by the recovery processor 56. The recovery processor 56 comprises a general processor operating pursuant to software control, a digital signal processor, hardware devices, such as dividers, multipliers, adders and subtractors, or RAM or ROM look-up tables appropriate for the reversal of one or more ultrasound image processes.

Reversal of any ultrasound image processing may be complete (i.e. all effects of one ultrasound image processing step removed from the ultrasound data) or partial (i.e. some of the effects of the ultrasound image process are removed from the ultrasound data). Some ultrasound image processing operations are fully reversible and others are only partially reversible. For example, application of a post-processing curve and persistence using an IIR filter are completely reversible. Some spatial filtering, dynamic range or log compression alteration, gain compensation (e.g. reversal limited by quantization) and histogram equalization are partially reversible. Some ultrasound image processes may not be reversible, such as some forms of dynamic range alteration, threshholding, and filtering that eliminates a signal component at a frequency. Preferably, ultrasound data provided to the recovery processor 56 has not been subjected to nonreversible ultrasound image processes. In alternate embodiments, the ultrasound data provided to the recovery processor 56 has been subjected to one or more nonreversible ultrasound image processes.

Figure 3:
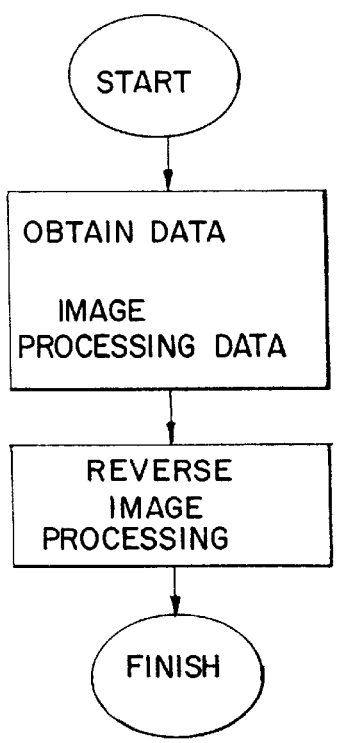
FIG. 3 is a flow chart representing a medical diagnostic ultrasound method for processing ultrasound data.

Referring to FIG. 3, a flow chart representing the reversal process is shown. In step 70, ultrasound data has been subjected to one or more ultrasound image processes is obtained. In step 72, one or more of the ultrasound image processes are reversed. Reversal may be partial or complete.

One or more of various gain processes may be reversed. Reversal is preferably performed as a function of the ultrasound image processing parameters provided with the frame of ultrasound data. The system 50 or the user may select complete reversal or partial reversal of ultrasound image gain processing.

Focal gain compensation and/or depth dependent gain compensation may be reversed as a function of the respective parameters. Recovered actual acoustical ultrasound signal levels (e.g. pre-processing) may allow quantification to be more reliably determined. An amount of gain desired for removal associated with each spatial location within the frame of ultrasound data is determined from the gain parameters. The amount of gain is used to either multiply, divide or otherwise weight the ultrasound data for removal of effects of gain compensation.

Dynamic range adjustment processing may be reversed. For reversal, the ultrasound data provided preferably was altered to have a higher dynamic range than is generally desired. For example, ultrasound data associated with an 80 dB dynamic range is input to the recovery processor 56. The previous dynamic range may be provided as the ultrasound image processing parameter. The current (i.e. desired) dynamic range may also be selected. The recovery processor 56 outputs ultrasound data with a lesser dynamic range, such as 60 dB. Alternatively, an image with a higher dynamic range is produced, but mapping to the entire gray scale range may be limited. For this reversal to 60 dB of dynamic range, the lower 20 dB of the input ultrasound data may be removed and a linear transform applied. For 8-bit data, a 255 value maps to a 255 output value and a 64 value outputs to a 0 value. Other linear or nonlinear transforms may be provided.

The recovery processor 56 may reverse the effects of the application of a post-processing curve or mapping. The post-processing curve or map used to process the ultrasound data is inversed for reversing the post-processing curve or mapping. For example, and referring to FIG. 4, a post-processing curve and its inverse are shown. The post-processing curve or map or the inverse are provided as the ultrasound image process parameter. The reverse curve is determined by reflecting about y=x. Using a processor or a look-up table, the ultrasound data values are used as inputs to determine an appropriate output based on the reversed curve.

The effects of persistence filtering may be reversed. Ultrasound data representative of ultrasound data prior to persistence processing is recovered. The reversal may be partial or complete. The recovered ultrasound data more closely represents the ultrasound data prior to persistence ultrasound image processing. By reversing persistence processing, the effects of persistence processing are reduced.

For IIR persistence processing, the ultrasound data input into the process is determined from the ultrasound data output by the persistence process and the persistence processing parameter or filter coefficient, $\alpha$. Using equation 1 above and solving for the input frame of ultrasound data $I_{in}$:

$$I_{in}(i) = \frac{I_{out}(i) - \alpha * I_{out}(i-1)}{(1-\alpha)} \quad (2)$$

Where the persistence processing parameter ($\alpha$) is known, a sequence of frames of ultrasound data are used to recover the input frames of ultrasound data, reversing the persistence processing. In order to reduce the effects of persistence without completely reversing the persistence processing, a smaller alpha may be used for reversal than was used for the original persistence processing (i.e. recovering frames of ultrasound data associated with some but less persistence).

Where the persistence parameter is adaptive, the recovery processor 56 applies an adaptive persistence parameter for reversing the persistence processing. For example, where the persistence parameter varies as a function of the frame rate, the recovery processor 56 likewise varies the persistence parameter as a function of the known frame rate.

If the persistence processing parameter is unknowns the parameter is estimated. The coefficient is assumed to be within a range, such as 0.1 to 0.8. Frames of ultrasound data are calculated using different values of the coefficient within the range. Preferably, the possible discrete values of $\alpha$ are known and used for calculating the frames of ultrasound data. The calculated frames of ultrasound data are used to estimate the actual coefficient value. The edginess, high-frequency spatial changes or speckle for each calculated frame of ultrasound data is used for determining the proper coefficient. A coefficient associated with the most edgy or sharpest speckle pattern of the calculated frames of ultrasound data is selected as the estimated coefficient, and the corresponding calculated frame of ultrasound data is selected as the recovered frame of ultrasound data.

The selection of the recovered frame of ultrasound data with the sharpest speckle is performed in one of various ways. In one method, the calculated frames of ultrasound data are used to generate displays, and the user selects the calculated frame of ultrasound data associated with the sharpest speckle pattern.

In preferred embodiments, the recovered frame of ultrasound data and the corresponding estimated parameter are selected automatically by the system 50, such as by the recovery processor 56. In one embodiment, a spatial frequency of the calculated frames of ultrasound data is measured. Spatial frequency is measured along an arbitrary line, a scanline, a depth line, a plurality of such lines or within one or more two- or three-dimensional regions. The calculated frame of data with the highest spatial frequency components or high frequency components that occur in the greatest number or spatial locations is selected as the recovered frame of ultrasound data. To determine the number or high-frequency components or the relative intensity of high spatial frequencies, the calculated frames of ultrasound data are frequency transformed using fast Fourier transforms or discrete cosine transforms. The discrete cosine transform operates on real data, and the fast Fourier transform may operate on complex data. Other transforms may be used. For discrete cosine transforms, high performance specialized hardware may be available, such as hardware for JPEG encoding. General processors, such as Intel Pentium processors with optimized machine instructions, (e.g. MMX) may also be used to rapidly perform transform calculations.

Another measure of the speckle or edginess of calculated frames of ultrasound data is based on gradient calculations. The difference between the amplitude of intensities of adjacent pixels is calculated for a line (arbitrary, horizontal or vertical), a region, multiple regions or the entire calculated frame of ultrasound data. These differences are summed. An edgy or high-speckle image is more likely to produce a greater sum of absolute differences that an image associated with any amount of persistence. The sum associated with each calculated frame of ultrasound data is then compared, and the filter coefficient associated with the highest sum is selected as the estimate. The corresponding calculated frame of ultrasound data is selected as the recovered frame of ultrasound data.

Another method for estimating the filter coefficient as a function of speckle and selecting the recovered frame of ultrasound data includes one of or both of the previously discussed methods. A sequence of calculated frames of ultrasound data associated with different possible filter coefficients are obtained. For any given frame of ultrasound data within the sequence, a plurality of calculated frames of data associated with a respective plurality of possible filter coefficient values are obtained. The intensity of the high-frequency components or the sum of absolute differences is determined for each of the plurality calculated frames of ultrasound data. A plot of the sum of absolute differences or the intensity of the high frequency components as a function of the possible filter coefficient is plotted for each calculated sequence. A subsampling of frames may be used. Assuming the frames of ultrasound data have approximately similar spatial frequency components, the curves converge at one particular filter coefficient value. That filter coefficient value is selected as the estimate, and the corresponding calculated frames of ultrasound data are selected as a sequence of recovered frames of ultrasound data. The above described method is preferably used in situations where the filter coefficient is likely a high value.

Other methods for estimating the filter coefficient may be used. For example, methods including two or more different techniques may be combined for more accurate estimation. The search for estimating the filter coefficient may be iterative. For example, a course search through fewer than all the possible filter coefficients may be performed. A fine search of additional possible filter coefficients is then performed for filter coefficient values near the previously estimated filter coefficient from the course search. As another example, a quadratic curve has a function of the sum of absolute differences, intensity of frequency components, or other indicators as a function of the possible filter coefficients is determined. The optimum filter coefficient is selected as a function of the predicted maximum of the quadratic curve. The filter coefficient may be estimated throughout a sequence of frames of ultrasound data or based on a sampling from within the sequence of frames of ultrasound data. Where the filtering coefficient likely varied as a function of time, the filtering coefficient is more frequently estimated during the sequence. Likewise, the filtering coefficient may be estimated as a function of location within one or more of the frames of ultrasound data to account for spatially varying, filter coefficients.

The recovered frame of ultrasound data associated with the estimated filter coefficient is saved or transmitted for further processing. In alternative embodiments, a calculated frame of ultrasound data associated with a different filter coefficient is selected so that the recovered frame of ultrasound data is associated with some but less persistence. As used herein, recovery frames of data include ultrasound data associated with substantially absolute reversal and ultrasound data associated with a partial reversal.

Spatial filtering and FIR persistence filtering ultrasound image processing may be reversed. Preferably, the spatial filtering or FIR persistence filtering did not eliminate frequency components of the ultrasound data. For reversal, an inverse of the frequency response of the filter is determined and applied to the ultrasound data. For example, the frequency response of the FIR filter is obtained as a function of the filtering parameter. The magnitude of frequency components that have been reduced is increased in the spectral domain to compensate for the reduction. A FIR filter is designed to produce the desired transformation of the ultrasound data for recovery.

Histogram equalization ultrasound image processing may be reversed. For example, if the histogram equalization is performed with a forward mapping transformation, the reverse operation is performed. An inverted transform is derived from the histogram forward mapping transform (e.g., the mapping functions inverse is determined) and is applied to provide for a lesser range of gray scale values.

Other ultrasound imaging processes may be reversed, either in part or wholly. Any of the various processes and associated parameters may vary as a function of time or location. Spatial or temporal variations in the ultrasound image processing may not be or may be minimally accounted for to recover frames of ultrasound data. A recovered frame of ultrasound data output by the recovery processor 56 may be associated with reversal of only one of a plurality of ultrasound imaging processes previously performed on the ultrasound data. In alternative embodiments, all or a subset of all of the ultrasound image processes are reversed. Some or all of the ultrasound image processing may be partially reversed.

In one preferred embodiment ultrasound data associated with motion detection is sent separately from ultrasound data associated with B-mode detection. Processes associated with each type of ultrasound data may be reversed independently of each other. Separate filter coefficients or ultrasound processing parameters may be determined for each of motion related and B-mode related ultrasound data. In alternate embodiments, the motion detected ultrasound data and B-mode data are combined, such as associated with a color Doppler overlay of a gray scale B-mode image. Preferably, the combined ultrasound data is separated prior to reversing any of the ultrasound image processing. One way of performing color separation or separation of this data is disclosed in U.S. application Ser. No. 09/196,986, filed Nov. 20, 1998, the disclosure of which is incorporated herein by reference. A color superimposing step can be used which mixes Doppler Color and B-mode speckle. Thereafter, the B-mode speckle is processed by referring to the Color lookup table and inferring the underlying B-mode value. If necessary, the B-mode values are rescaled if they were scaled during the color mapping process.

In embodiments where the ultrasound image parameter is estimated from the ultrasound data, the ultrasound imaging parameter may be estimated from combined B-mode and motion ultrasound data as a function of subregions. For example, the filter coefficient for IIR persistence processing is determined as a function of an area represented by B-mode only ultrasound data. In alternative embodiments, the motion or color portion of the ultrasound data may be used. For reversing ultrasound image processing using known parameters, frames of combined B-mode and motion ultrasound data may be recovered regardless of the type of ultrasound data.

The recovered frames of ultrasound data are used to generate a display. In a preferred embodiment, recovered frames of ultrasound data are stored and/or further processed prior to generation of an image on the display 62. For example, the recovered frames of ultrasound data are stored in the memory 58. The memory 58 comprises a RAM, a hard drive, a removable storage medium or other memory devices for storing ultrasound data.

The image processor accesses the recovered frames of ultrasound data, such as from the memory 58, and performs ultrasound image processing on the recovered frames of ultrasound data. The image processor 60 comprises one or more digital signal processors, general processors operating pursuant to software control, or other hardware devices such as the devices discussed above with respect to each type of ultrasound image processing.

The image processor 60 operates in response to instructions from the control computer 68. Based on user input, the recovered frames of ultrasound data are processed to generate an image. By recovering the frames of ultrasound data, different amounts and types of ultrasound image processing may be applied to generate a different image based on the same ultrasound data.

Alternatively or additionally, the reversed ultrasound image processing applied by the recovery processor 56 is responsive to the user input through the control computer 68 in order to control the amount of reversal and/or types of ultrasound image process reversed. For example, instead of completely reversing IIR persistence processing, a recovered frame of ultrasound data associated with partial reversal is obtained. The user controls the amount of persistence associated with the recovered frame of ultrasound data. The recovered frame of ultrasound data may then be further persisted or have no persistence processing applied by the image processor 60 prior to generation of an image on the display 62.

In order to provide the user with the maximum versatility, the image processor 60 is operable to obtain the recovered frames of ultrasound data and apply ultrasound image processing in different ways. The user views an image different from the original image in an attempt to better identify diagnostic information.

In one embodiment, the sequence of ultrasound data represented by block 52 comprises ultrasound data subjected to some ultrasound image processing, but not other ultrasound image processing. For example, ultrasound data associated with log compression, focal gain compensation, and persistence processing is provided without having been subjected to spatial filtering, post-processing transformation and depth gain compensation. The recovery processor 56 reverses one or more of the previously used ultrasound image processes, such as persistence processing. The image processor 60 applies one or more ultrasound image processes, such as spatial filtering and persistence filtering.

In alternative embodiments, the frames of ultrasound data bypass the recovery processor 56. The image processor applies further ultrasound image processing. The image processor 60 may generate an image that is identical to or different than any previous images, such as using the ultrasound image processing parameters to recreate the same image that was created previously. An image responsive to different ultrasound image processing may also be created.

In one embodiment, the user re-persists the recovered frames of ultrasound data without necessitating a further scan. By applying persistence to recovered frames of ultrasound data, FIR or IIR persistence filtering is used. Versatile FIR persistence filtering allows filtering based on a frame before and after the frame of interest within the sequence. For example, a five-tap FIR filter is used, such as represented by:

$$I_{out}(i)=W(1)*I_{in}(i-2)+W(2)*I_{in}(i-1)+W(3)*I_{in}(i)+W(4)*I_{in}(i+1)+W(5)*I_{in}(i+1),$$

where W(1.5) define the FIR filter coefficients. For example, the filter coefficients are [0.1, 0.2, 0.4, 0.2, 0.1]. The user preferably selects the number of taps of the filter and the shape of the filter (e.g. the weights). For IIR persistence filtering, the user selects the filter coefficient, $\alpha$. Preferably, the user can select between an FIR and an IIR filter. For IIR filtering, a high value filter coefficient provides a higher amount of contribution from previous frames of ultrasound data, and a low value provides for less persistence. For FIR filtering, a user perceived more persistence may be obtained using a fewer number of frames than with an IIR filter. By using a fewer number of frames for FIR persistence filtering, the contribution from more temporally spaced frames of data is reduced or eliminated.

For further enhancement of re-persistence, the recovered frames of ultrasound data are aligned or substantially aligned prior to repersisting. Relative movement between the transducer and the target results in frames of ultrasound data representing slightly offset or partially different regions of the target. The motion between frames of ultrasound data associated with misalignment is detected and compensated for prior to persistence or re-persistence. For example, the minimum sum of absolute differences between two frames of ultrasound data rotated and translated to different positions relative to each other is determined. The translation and rotation associated with the minimum sum of absolute differences indicates the proper alignment of the frames of ultrasound data. Further examples are provided in U.S. application Ser. No. 09/199,945, filed Nov. 25, 1998 and U.S. application Ser. No. 09/328,113 for a Medical Diagnostic Ultrasound System And Method For Versatile Processing, filed herewith, the disclosures of which are incorporated herein by reference. As another example, a position sensor is used to determine translation in range and in azimuth dimensions and rotation. For example, a magnetic sensor is used. In this embodiment, the relative rotation of the frames of data may also be determined from the position sensor. Other correlation techniques may be used. Based on the positional information, the frames of ultrasound data are aligned using registers or other suitable memory devices, such as the memory 58. Alternatively, the frames of data are spatially compounded without alignment in one, two or all of the range dimension, the azimuth dimension and rotation.

In one embodiment, the frames of ultrasound data are aligned as a function of a region of interest. Image distortion may limit the ability to determine the correlation between two entire frames of data. The user manually selects or the system 50 automatically selects a region of interest. In alternative embodiments, the user selects a point or points, and the system 50 defines a region of interest around or centered on the point or points. Preferably, the region of interest is at least two times the speckle period in each dimension. The speckle period varies as a function of transducer geometry and frequency. For example, transmitting at a 5 MHz frequency with a transducer having a 4 centimeter aperture provides a 2 millimeter wide by 1 millimeter high speckle period. The speckle period may be measured or estimated as a function of the transducer geometry and frequency. Alternatively, the size of the region of interest is determined as a function of common usage, such as using a 10×10 or 20×20 block of pixels. For efficient processing, a 32×32 or 48×48 pixel area in the middle of the image region may be used for determining an amount of correlation, such as using auto correlation or the minimum sum of absolute differences. Other locations within the image, such as the top or at the bottom of the image or both, may be used. Smaller or larger region of interests, including regions of interest less than two speckle periods wide or high, are possible.

The selected region of interest (ROI) is used to determine the correlation and corresponding translation in range, azimuth and/or rotation between any two frames of ultrasound data. Further, as the image with the ROI moves, the ROI defining box is moved as appropriate to designate the same physical area of the patient. Alternatively, the region of interest is emphasized over the other regions within the frames of data, such as applying weighted averaging to correlation calculations. A higher weight is applied to the correlation value for the region of interest than to correlation values associated with other regions. The translation and rotation are then determined as a function of the entire image with an emphasis on the region of interest. Any one of various correlation or cross-correlation functions may be used. Various coarse followed by fine or just coarse or just fine searching may be used for determining the correlations.

In addition to persistence ultrasound image processing, other ultrasound image processing is provided by the image processor 60. These ultrasound imaging processes may be different or the same as the ultrasound image processing discussed above. For example, a post-processing transform as a function of a curve or map is provided. The user is offered a menu of various curves or maps. Alternatively, the system 50 automatically selects a particular map or curve. The curve may provide for clipping or thresholding. As another example, the user is offered depth gain control through a graphic user interface or analog potentiometers. In alternative embodiments, the system 50 determines an amount of depth gain compensation. As yet another example, the ultrasound data is filtered, such as spatial filtering. The user may select or the system 50 may automatically determine one or more filters, such as edge enhancing filters (e.g. high pass filters), smoothing filters (e.g. low pass filters), contrast enhancing filters (e.g. filters discussed in U.S. Pat. No. 5,479,926), linear or nonlinear filtering (e.g. thresholding), and/or median filtering. Another example is histogram equalization for a contrast enhancement. The histogram equalization calculation may be performed on the first frame of a sequence, a subset of the frames of a sequence, or for every frame within a sequence.

The ultrasound data resulting from subjection of the recovered frames of ultrasound data to ultrasound image processing may be used for various ultrasound diagnostic aids. For example, an image is generated as a function of the frames of ultrasound data. A B-mode, a motion, or a combination B-mode and motion image or sequence of images are generated.

Where the sequence of frames of ultrasound data represents a 3-dimensional volume, the ultrasound data may be combined or aligned to form a spaced dataset. Preferably, information representing the spatial distribution of each of the frames of ultrasound data relative to the other frames of ultrasound data is provided. For example, magnetic positioners, accelerometers, optical detection devices, acoustic spark gap devices, motorized translation devices and registration as a function of correlation of the frames of ultrasound data, and other techniques may be used for determining translation and rotation between the frames of ultrasound data. In one embodiment, the translation and rotation information is estimated or assumed. The volume dataset may be used to generate 2-dimensional representations, such as shaded surface rendering, volume alpha blending, maximum intensity projection, minimum intensity projection, or arbitrary 2-dimensional plane within the 3-dimensional volume dataset (e.g. multi-planar reformatting (MPR)).

In addition to imaging, the ultrasound data may be quantified. Regions of interest are selected by the user or automatically identified by the system 50 using the processed ultrasound data. Combinations of user input and automation may be used for identifying a region of interest. Quantifications are calculated using the identified regions or interest or other selection techniques. For example, the area of a region of interest may be calculated. Summation of B-mode intensities or some other quantity, such as motion information, may be calculated for a region of interest. Based on any focal gain and other gain compensations, an integration of values accounting for original echo signal levels and any nonlinear operations is calculated. In one example, the walls of a chamber of the heart are outlined or selected as the region of interest. All the signals associated with the presence of an injected contrast agent are integrated. A wash-out curve or wash-in curve showing the rate of contrast agent entry or ejection from the chamber is produced. Other quantities may be calculated.

The ultrasound data used for ultrasound image processing is associated with the broadest range of data. For example, signal components from the echo signals at transmitted fundamental frequencies or at a harmonic of the fundamental frequencies may be used. The echo signals may be responsive to tissue, fluids and optionally contrast agents. Color Doppler, such as energy or velocity, imaging may be used. The ultrasound data may be corrected for motion related distortion, such as disclosed in U.S. Pat. No. 5,873,830. This correction may be reversed and/or applied after reversal of other image processing.

While the invention has been described above by reference to various embodiments, it will be understood that many changes and modifications can be made without departing from the scope of the invention. For example, ultrasound image processing parameters that vary as a function of time or spatial location may be used and estimated. The reversal and subsequent different amount of ultrasound image processing steps may be combined or performed as one operation. Different ultrasound image processes may be used, including ultrasound image processes developed in the future. The ultrasound data may comprise data associated with one or more of data at fundamental frequencies, data at harmonics of the fundamental frequencies, data reflected from tissue, data reflected from contrast agents, gray scale data, color Doppler variance data, color Doppler energy data, color Doppler velocity data, color Doppler tissue data, spectral Doppler data and M-mode data.

It is therefore intended that the foregoing detailed description be understood as an illustration of the presently preferred embodiments of the invention, and not as a definition of the invention. It is only the following claims, including all equivalents, that are intended to find the scope of this invention.

What is claimed is:

1. A medical diagnostic ultrasound method for persistence processing, the method comprising the steps of:
   (a) obtaining at least two frames of persisted ultrasound data; and
   (b) recovering at least two frames of reduced persistence ultrasound data from the at least two frames of persisted ultrasound data.

2. The method of claim 1 where step (b) comprises reducing some of the effects of persistence from the at least two frames of persisted ultrasound data.

3. The method of claim 1 wherein step (b) comprises recovering the at least two frames of reduced persistence ultrasound data as at least two frames of non-persisted ultrasound data.

4. The method of claim 1 further comprising:
   (c) generating the at least two frames of persisted ultrasound data with an infinite impulse response filter characterized by a coefficient; and
   wherein the coefficient is known and step (b) is responsive to the known coefficient.

5. The method of claim 1 further comprising:
   repeating steps (a) and (b) wherein the recovery of step (b) is responsive to at least one time varying persistence filter characteristic.

6. The method of claim 1 further comprising:
   (c) generating the at two frames of persisted ultrasound data with an infinite impulse response filter characterized by a coefficient; and
   (d) estimating a value of the coefficient from the at least two frames of persisted ultrasound data;
   wherein step (b) is responsive to the estimated value.

7. The method of claim 6 wherein step (d) comprises:
   (d1) recovering a plurality of recovery frames of data as a function of a respective plurality of different filter coefficients;
   (d2) determining a measure of image speckle for each of the plurality of recovery frames of data; and
   (d3) selecting the filter coefficient corresponding to the recovery frame of data as the estimated value.

8. The method of claim 7 wherein step (d2) comprises estimating a spatial frequency characteristic.

9. The method of claim 7 wherein:
   step (d2) comprises:
     determining a gradient frame of data for each of the plurality of recovery frames of data;
     summing gradient values within each of the gradient frames of data; and
   step (d3) comprises selecting the filter coefficient corresponding to the recovery frame of data with the greatest sum of gradient values.

10. The method of claim 7 wherein step (d2) comprises:
    plotting a plurality of curves, each curve a function of one of the plurality of recovery frames and a characteristic selected from the group consisting of: spatial frequency and a sum of gradient values.

11. The method of claim 1 further comprising:
    (c) persisting the at least two frames of reduced persistence ultrasound data.

12. The method of claim 11 wherein step (c) comprises persisting the at least two frames of reduced persistence ultrasound data with a finite impulse response filter.

13. The method of 11 further comprising:
(d) aligning the at least two frames of reduced persistence ultrasound data prior to performing step (c).

14. A medical diagnostic ultrasound system for persistence processing, the system comprising:
a memory storing at least two frames of persisted ultrasound data; and
a processor for recovering at least two frames of reduced persistence ultrasound data from the at least two frames of persisted ultrasound data.

15. The system of claim 14 further comprising:
an infinite impulse response filter characterized by a coefficient for generating the at least two frames of persisted ultrasound data; and
wherein the coefficient is provided to the processor and the processor is operable to recover in responsive to the known coefficient.

16. The system of claim 14 further comprising:
an infinite impulse response filter characterized by a coefficient for generating the at least two frames of persisted ultrasound data; and
wherein the processor is operable to estimate a value of the coefficient from the at least two frames of persisted ultrasound data and operable to recover the at least two frames of reduced persistence ultrasound data as a function of the estimated value.

17. The system of claim 14 further comprising:
a finite impulse response filter comprising two inputs for receiving the at least two frames of reduced persistence ultrasound data.

* * * * *

UNITED STATES PATENT AND TRADEMARK OFFICE
CERTIFICATE OF CORRECTION

PATENT NO. : 6,352,511 B1
DATED : March 5, 2002
INVENTOR(S) : John A. Hossack et al.

It is certified that error appears in the above-identified patent and that said Letters Patent is hereby corrected as shown below:

Column 8,
Line 49, delete "data." and substitute -- data, -- in its place.

Column 11,
Line 5, delete "unknowns" and substitute -- unknown -- in its place.

Signed and Sealed this

Twenty-ninth Day of April, 2003

JAMES E. ROGAN
*Director of the United States Patent and Trademark Office*